United States Patent [19]
Gerhold

[11] Patent Number: 6,030,788
[45] Date of Patent: Feb. 29, 2000

[54] CYCLIN-DEPENDENT PROTEIN KINASE

[75] Inventor: David L. Gerhold, Lansdale, Pa.

[73] Assignee: Merck & Co., Inc., Rahway, N.J.

[21] Appl. No.: 09/248,137

[22] Filed: Feb. 10, 1999

Related U.S. Application Data

[62] Division of application No. 09/018,576, Feb. 5, 1998, Pat. No. 5,968,800.
[60] Provisional application No. 60/037,855, Feb. 7, 1997.

[51] Int. Cl.$^7$ .............................. C12Q 1/68; C12N 9/12; C12N 1/20; C12N 15/00; C12N 5/00
[52] U.S. Cl. .......................... 435/6; 435/194; 435/320.1; 435/325; 435/252.3; 530/350
[58] Field of Search ........................... 435/194, 6, 320.1, 435/325, 252.3; 530/350

[56] References Cited

PUBLICATIONS

Kobayashi et al. "Identification of the Domains in Cyclic A Required for Binding to, and Activation of, p34 (cdc2) and p32(cdk2) Protein Kinase Subunits", Molecular Bioblogy of the Cell, vol. 3, 1279–1294, Nov. 1992.

Lees et al. "Sequences within the Conserved Cyclic Box of Human Cyclin A Are Sufficient for Binding to and Activation of cdc2 Kinase", Molecular and Cellular Biology, vol. 13 Feb. 1993, pp 1194–1201.

Poon et al. "Cell cycle regulation of the p34(cdc2)/p33(cdk2)–activating kinase p40(MO15)", Jour. of Cell Science 107, 2789–2799 (1994).

Fisher et al. "A Novel Cyclin Associates with MO15/CDK7 to Form the CDK–Activating Kinase", Cell, vol. 78, pp 713–724 Aug. 26, 1994.

Morgan et al. "Principles of CDK regulation", Nature, vol. 374, pp 131–134 Mar. 9, 1995.

van der Heuvel et al. "Distinct Roles for Cyclin–Dependent Kinases in Cell Cycle Control", Science, vol. 262, Dec. 24, 1993.

Wilson, 1995, The Wash U–Merck EST Project, dbEST 277665, GenBank Acc. No. H17727.

Pines, Reaching for a role for the Cks protiens; Current Biology; 1996, vol. 6, No. 11; pp 1399–1402.

Morgan, The dynamics of cyclin dependent kkinase structure; Current Opinion in Cell Biology; 1996; 8: 767–772.

Brambilla et al., Molecular cloning of PISSLRE, a novel putative member of the cdk family of protein serine/threonine kinases; Oncogene, vol. 9, pp 3037–3041, 1994.

*Primary Examiner*—Ponnathapu Achutamurthy
*Assistant Examiner*—M. Monshipouri
*Attorney, Agent, or Firm*—J. Mark Hand; Jack L. Tribble

[57] ABSTRACT

An isolated nucleic acid molecule is disclosed which encodes a novel human cyclin-dependent kinase (CDK) which comprises a novel cyclin binding domain signature sequence and lacks several heretofore conserved amino acid residues involved in regulation of the cdk/cyclin complex. Associated proteins and biologically active mutant forms are also disclosed.

6 Claims, 5 Drawing Sheets

```
   1 GAAAAGGCGC AGTGGGGCCC GGAGCTGTCA CCCCTGACTC GACGCAGCTT
  51 CCGTTCTCCT GGTGACGTCG CCTACAGGAA CCGCCCCAGT GGTCAGCTGC
 101 CGCGCTGTTG CTAGGCAACA GCGTGCGAGC TCAGATCAGC GTGGGGTGGA
 151 GGAGAAGTGG AGTTTGGAAG TTCAGGGGCA CAGGGGCACA GGCCCACGAC
 201 TGCAGCGGGA TGGACCAGTA CTGCATCCTG GGCCGCATCG GGGAGGGCGC
 251 CCACGGCATC GTCTTCAAGG CCAAGCACGT GGAGACTGGC GAGATAGTTG
 301 CCCTCAAGAA GGTGGCCCTA AGGCGGTTGG AAGACGGCTT CCCTAACCAG
 351 GCCCTGCGGG AGATTAAGGC TCTGCAGGAG ATGGAGGACA ATCAGTATGT
 401 GGTACAACTG AAGGCTGTGT TCCCACACGG TGGAGGCTTT GTGCTGGCCT
 451 TTGAGTTCAT GCTGTCGGAT CTGGCCGAGG TGGTGCGCCA TGCCCAGAGG
 501 CCACTAGCCC AGGCACAGGT CAAGAGCTAC CTGCAGATGC TGCTCAAGGG
 551 TGTCGCCTTC TGCCATGCCA ACAACATTGT ACATCGGGAC CTGAAACCTG
 601 CCAACCTGCT CATCAGCGCC TCAGGCCAGC TCAAGATAGC GGACTTTGGC
 651 CTGGCTCGAG TCTTTTCCCC AGACGGCAGC CGCCTCTACA CACACCAGGT
 701 GGCCACCAGG TCTGTGGGCT GCATCATGGG GGAGCTGTTG AATGGGTCCC
 751 CCCTTTTCCC GGGCAAGAAC GATATTGAAC AGCTTTGCTA TGTGCTTCGC
 801 ATCTTGGGCA CCCCAAACCC TCAAGTCTGG CCGGAGCTCA CTGAGCTGCC
 851 GGACTACAAC AAGATCTCCT TTAAGGAGCA GGTGCCCATG CCCCTGGAGG
 901 AGGTGCTGCC TGACGTCTCT CCCCAGGCAT TGGATCTGCT GGGTCAATTC
 951 CTTCTCTACC CTCCTCACCA GCGCATCGCA GCTTCCAAGG CTCTCCTCCA
1001 TCAGTACTTC TTCACAGCTC CCCTGCCTGC CCATCCATCT GAGCTGCCGA
1051 TTCCTCAGCG TCTAGGGGGA CCTGCCCCCA AGGCCCATCC AGGGCCCCCC
1101 CACATCCATG ACTTCCACGT GGACCGGCCT CTTGAGGAGT CGCTGTTGAA
1151 CCCAGAGCTG ATTCGGCCCT TCATCCTGGA GGGGTGAGAA GTTGGCCCTG
1201 GTCCCGTCTG CCTGCTCCTC AGGACCACTC AGTCCACCTG TTCCTCTGCC
1251 ACCTGCCTGG CTTCACCCTC CAAGGCCTCC CCATGGCCAC AGTGGGCCCA
1301 CACCACACCC TGCCCCTTAG CCCTTGCGAG GGTTGGTCTC GAGGCAGAGG
1351 TCATGTTCCC AGCCAAGAGT ATGAGAACAT CCAGTCGAGC AGAGGAGATT
1401 CATGGCCTGT GCTCGGTGAG CCTTACCTTC TGTGTGCTAC TGACGTACCC
1451 ATCAGGACAG TGAGCTCTGC TGCCAGTCAA GGCCTGCATA TGCAGAATGA
1501 CGATGCCTGC CTTGGTGCTG CTTCCCCGAG TGCTGCCTCC TGGTCAAGGA
1551 GAAGTGCAGA GAGTAAGGTG TCCTTATGTT GGAAACTCAA GTGGAAGGAA
1601 GATTTGGTTT GGTTTTATTC TCAGAGCCAT TAAACACTAG TTCAGTATGT
1651 GAGATATAGA TTCTAAAAAC CTCAGGTGGC TCTGCCTTAT GTCTGTTCCT
1701 CCTTCATTTC TCTCAAGGGA AATGGCTAAG GTGGCATTGT CTCATGGCTC
1751 TCGTTTTTGG GGTCATGGGG AGGGTAGCAC CAGGCATAGC CACTTTTGCC
1801 CTGAGGGACT CCTGTGTGCT TCACATCACT GAGCACTCAT TTAGAAGTGA
1851 GGGAGACAGA AGTCTAGGCC CAGGGATGGC TCCAGTTGGG GATCCAGCAG
1901 GAGACCCTCT GCACATGAGG CTGGTTTACC AACATCTACT CCCTCAGGAT
1951 GAGCGTGAGC CAGAAGCAGC TGTGTATTTA AGGAAACAAG CGTTCCTGGA
2001 ATTAATTTAT AAATTTAATA AATCCCAATA TAATCCCAAA AAAAAAAAAA
2051 AAAAAATTCC TGCGGCCGCA AGGA ( SEQ ID NO.2)
```

FIG.1

1    MDQYCILGRI GEGAHGIVFK AKHVETGEIV ALKKVALRRL EDGFPNQALR

51   EIKALQEMED NQYVVQLKAV FPHGGGFVLA FEFMLSDLAE VVRHAQRPLA

101  QAQVKSYLQM LLKGVAFCHA NNIVHRDLKP ANLLISASGQ LKIADFGLAR

151  VFSPDGSRLY THQVATRSVG CIMGELLNGS PLFPGKNDIE QLCYVLRILG

201  TPNPQVWPEL TELPDYNKIS FKEQVPMPLE EVLPDVSPQA LDLLGQFLLY

251  PPHQRIAASK ALLHQYFFTA PLPAHPSELP IPQRLGGPAP KAHPGPPHIH

301  DFHVDRPLEE SLLNPELIRP FILEG* ( SEQ ID NO.3)

FIG.2

CYCLIN-DEPENDENT PROTEIN KINASE

CROSS-REFERENCE TO RELATED APPLICATIONS

This is a division of application Ser. No. 09/018,576 filed Feb. 5, 1998, U.S. Pat. No. 5,968,800 issued Oct. 19, 1999 which claims priority to provisional application U.S. Ser. No. 60/037,855 filed Feb. 7, 1997.

FIELD OF THE INVENTION

The present invention relates to an isolated nucleic acid molecule (polynucleotide) which encodes a novel human cyclin-dependent kinase (CDK) comprising a novel cyclin binding domain signature sequence and lacking several heretofore conserved amino acid residues involved in regulation of the cdk/cyclin complex. The present invention also relates to associated human CDK proteins and human CDK mutant proteins.

BACKGROUND OF THE INVENTION

Cell growth and division in eukaryotic organisms is mediated through the cell cycle. The cell cycle consists of two major events separated by two central gap phases. DNA synthesis and replication occur during the S phase while mitosis occurs during the M phase. A first gap phase, called $G_1$, which occurs between the M phase and the S phase, allows for accumulation of enzymes and other compounds necessary to drive DNA synthesis and genome replication. A second gap phase, called $G_2$, occurs between the S phase and the M phase, allowing for controls to check for proper DNA replication prior to committing to cell division.

Transition to and passage through the four stages of the eukaryotic cell cycle are regulated by a family of cyclin-dependent protein kinases (CDKs). Activation of a CDK requires binding to a cyclin regulatory subunit, and in the case of CDK1–CDK6, phosophorylation of threonine 160/161 (Thr160/161). These CDKs contain a cyclin binding site near the amino terminal portion of the protein. The activated CDK/cyclin complex phosphorylates proteins involved in various stages of the cell cycle.

The family of cyclin proteins may generally be classified as either $G_1$ cyclins or mitotic cyclins, depending on peak expression levels. A CDK may bind a subset of cyclins. For example, CDK4 is known to bind cyclin D1 or cyclin D3 whereas CDK2 is known to bind cyclin A, cyclin B1, cyclin B2, cyclin B3 and cyclin E. The vertebrate cyclins show homology within a region of approximately 100 amino acids, referred to as the cyclin box. This region is responsible for CDK binding and activity (Kobayashi, et al., 1992, *Molec. Biol. Cell.* 3: 1279–1294; Lees, et al., 1993, *Molec. Cell. Biol.*, 1993, 13: 1194–1201). It is this region of the cyclin protein which interacts with the cyclin binding domain of a respective CDK protein.

Complete activation of a known CDK/cyclin complex requires phosphorlyation by a CDK-Activating Kinase (CAK). The vertebrate CAK has been identified as a CDK/cyclin complex, more specifically CDK7/cyclinH (Fisher and Morgan, 1994, *Cell* 78: 713–724). The CAK enzyme comprises a threonine 170 residue (in human CDK7) which has been shown to be required for optimal activity (Poon, et al., 1994, *J. Cell Sci.* 107: 2789–2799; Fisher and Morgan, 1994, *Cell* 78: 713–724).

Inhibition of CDK/cyclin complexes are thought to occur via phosphorylation at threonine 14 (Thr14) and/or tyrosine 15 (Tyr15) of the CDK subunit. The Wee1 kinase has been suggested as either a Thr14 kinase or as a Thr14 and Tyr15 kinase. Additionally, CDC25 is thought to be a dual kinase targeting both Thr14 and/or Tyr15 (Morgan, 1995, *Nature* 374: 131–134).

It would be advantageous to identify a gene encoding an additional CDK protein. A nucleic acid molecule expressing a CDK protein would be extremely useful in screening for compounds acting as a modulator of the cell cycle. Such a compound or compounds will be useful in controlling cell growth associated with cancer or immune cell proliferation. Additionally, the recombinant form of protein expressed from such a novel gene would be useful for an in vitro assay to determine specificity toward substrate proteins, inhibitors and cyclin activators. Additionally, an isolated and purified CDK10 cDNA which encodes CDK-10 or an active mutant thereof will also be useful for the recombinant production of large quantities of respective protein. The ability to produce large quantities of the protein would be useful for the production of a therapeutic agent comprising the CDK10 protein or a mutant such as the exemplified mutant disclosed herein. A therapeutic agent comprised of CDK10 protein would be useful in the treatment of cell cycle and/or CDK10 related diseases or conditions which are CDK10 responsive. The present invention addresses and meets this need.

SUMMARY OF THE INVENTION

The present invention relates to an isolated nucleic acid molecule (polynucleotide) which encodes a novel human cyclin-dependent kinase. This CDK comprises a novel cyclin binding domain signature sequence (Pro-Asn-Gln-Ala-Leu-Arg-Glu; SEQ ID NO:1), lacks Thr14 and/or Tyr15, and also lacks the T-loop domain containing the conserved Thr160/161 residue.

The present invention relates to biologically active fragments or mutants of a novel isolated nucleic acid molecule which encodes mRNA expressing a novel human cyclin-dependent kinase. Any such biologically active fragment and/or mutant will encode a protein or protein fragment comprising a novel cyclin binding domain signature sequence (Pro-Asn-Gln-Ala-Leu-Arg-Glu; SEQ ID NO:1), which lacks Thr14 and/or Tyr15 as well as a T-loop domain containing the conserved Thr160/161 residue. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use.

The isolated nucleic acid molecule of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

A preferred aspect of the present invention is disclosed in SEQ ID NO:11 and FIG. 1, a human DNA fragment which encodes the novel human cyclin-dependent kinase, CDK10.

The present invention also relates to a substantially purified novel cyclin-dependent kinase which comprises a novel cyclin binding domain signature sequence (Pro-Asn-Gln-Ala-Leu-Arg-Glu; SEQ ID NO:1), lacks Thr14 and Tyr15 which make up the conserved ATP binding motif of several known CKDs, and also lacks the T-loop domain containing the conserved Thr160/161 residue.

The present invention also relates to biologically active fragments and/or mutants of a novel cyclin-dependent kinase which comprises a novel cyclin binding domain signature sequence, lacks Thr14 and/or Tyr15 which make up the conserved ATP binding motif of known CKDs, and also lacks the T-loop domain containing the conserved Thr160/161 residue, including but not necessarily limited to amino acid substitutions, deletions, additions, amino terminal truncations and carboxy-terminal truncations such that these mutations provide for proteins or protein fragments of diagnostic, therapeutic or prophylactic use.

A preferred aspect of the present invention is disclosed in SEQ ID NO:3 and FIG. 2, the amino acid sequence of CDK10. The open reading frame of the CDK10 coding region runs from nucleotide 210 to nucleotide 1182 of SEQ ID NO:2.

Another preferred aspect of the present invention is disclosed in SEQ ID NO:11, wherein nucleotide 588 of the wild-type form (SEQ ID NO: 2) is mutated from "G" to "A".

Another preferred aspect of the present invention is the mutant protein, (CDK10-D127N), wherein nucleotide 588 of SEQ ID NO:11 is mutated from "G" to "A", as compared to the wild-type form (SEQ ID NO:2), which results in a change of Asp127 to Asn127 as compared to the wild-type amino acid sequence (SEQ ID NO:3), disclosed as SEQ ID NO:12.

The present invention also relates to methods of expressing the cyclin-dependent kinases disclosed herein, assays employing these cyclin-dependent kinases, cells expressing these cyclin-dependent kinases, and compounds identified through the use of these cyclin-dependent kinases, including modulators of the cyclin-dependents kinase either through direct contact with the cyclin-dependent kinase, an associated cyclin, or the CKD/cyclin complex. Such modulators identified in this process are useful as therapeutic agents for controlling cell growth or immune cell proliferation commonly associated with cancer.

DETAILED DESCRIPTION OF THE DRAWINGS

FIG. 1 shows the nucleotide sequence (SEQ ID NO:2) which comprises the full length cDNA encoding human CDK10.

FIG. 2 shows the amino acid sequence (SEQ ID NO:3) of human CDK10.

DETAILED DESCRIPTION OF THE INVENTION

Figure 3:
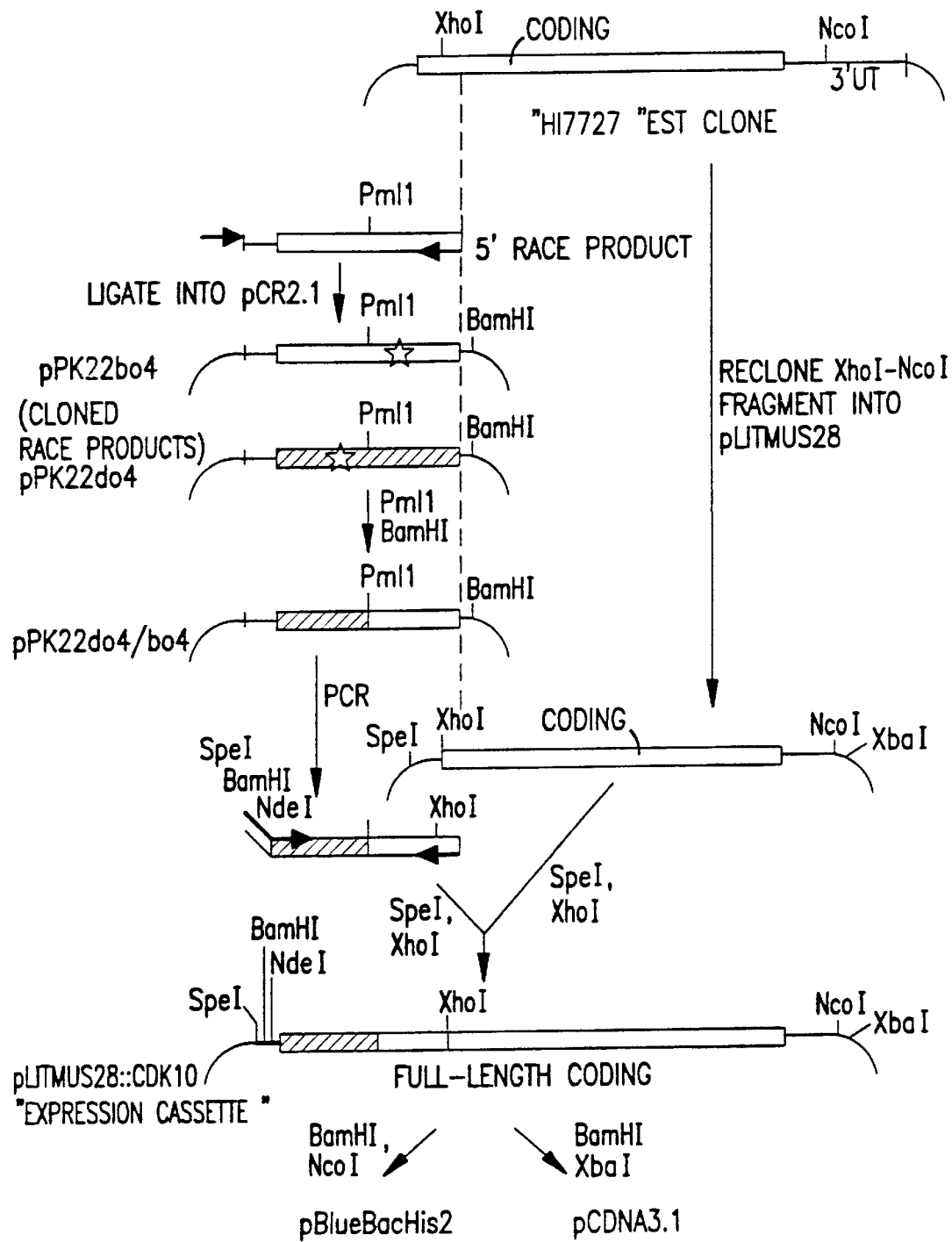
FIG. 3 shows the strategy utilized to generate a full-length DNA fragment encoding human CDK10.

The present invention relates to an isolated nucleic acid molecule (polynucleotide) which encodes a novel cyclin-dependent kinase which comprises a novel human cyclin binding domain (Pro-Asn-Gln-Ala-Leu-Arg-Glu; SEQ ID NO:1), lacks Thr14 and/or Tyr15 which make up the conserved ATP binding motif of known CDKS, and also lacks the T-loop domain containing the conserved Thr160/161 residue.

The present invention also relates to biologically active fragments and/or mutants of a novel isolated nucleic acid molecule which encode mRNA expressing a novel human cyclin-dependent kinase. Such a protein comprises a novel cyclin binding domain signature sequence (Pro-Asn-Gln-Ala-Leu-Arg-Glu; SEQ ID NO:1), lacks Thr14 and/or Tyr15, and also lack a T-loop domain containing the conserved Thr160/161 residue. The protein of the present invention includes but is not limited to nucleotide substitutions, deletions, additions, amino terminal truncations and carboxy-terminal truncations such that these mutations encode mRNA which express a protein or protein fragment of diagnostic, therapeutic or prophylactic use.

A preferred aspect of the present invention is disclosed in FIG. 1 and SEQ ID NO:2, a human cDNA encoding a novel cyclin-dependent kinase, CDK10, disclosed herein as:

```
GAAAAGGCGC AGTGGGGCCC GGAGCTATCA CCCCTGACTC GACGCAGCTT CCGTTCTCCT(SEQ ID NO:2)

GGTGACGTCG CCTACAGGAA CCGCCCCAGT GGTCAGCTGC CGCGCTGTTG CTAGGCAACA

GCGTGCGAGC TCAGATCAGC GTGGGGTGGA GGAGAAGTGG AGTTTGGAAG TTCAGGGGCA

CAGGGGCACA GGCCCACGAC TGCAGCGGGA TGGACCAGTA CTGCATCCTG GGCCGCATCG

GGGAGGGCGC CCACGGCATC GTCTTCAAGG CCAAGCACGT GGAGACTGGC GAGATAGTTG

CCCTCAAGAA GGTGGCCCTA AGGCGGTTGG AAGACGGCTT CCCTAACCAG GCCCTGCGGG

AGATTAAGGC TCTGCAGGAG ATGGAGGACA ATCAGTATGT GGTACAACTG AAGGCTGTGT

TCCCACACGG TGGAGGCTTT GTGCTGGCCT TTGAGTTCAT GCTGTCGGAT CTGGCCGAGG

TGGTGCGCCA TGCCCAGAGG CCACTAGCCC AGGCACAGGT CAAGAGCTAC CTGCAGATGC

TGCTCAAGGG TGTCGCCTTC TGCCATGCCA ACAACATTGT ACATCGGGAC CTGAAACCTG

CCAACCTGCT CATCAGCGCC TCAGGCCAGC TCAAGATAGC GGACTTTGGC CTGGCTCGAG

TCTTTTCCCC AGACGGCAGC CGCCTCTACA CACACCAGGT GGCCACCAGG TCTGTGGGCT

GCATCATGGG GGAGCTGTTG AATGGGTCCC CCCTTTTCCC GGGCAAGAAC GATATTGAAC

AGCTTTGCTA TGTGCTTCGC ATCTTGGGCA CCCCAAACCC TCAAGTCTGG CCGGAGCTCA

CTGAGCTGCC GGACTACAAC AAGATCTCCT TTAAGGAGCA GGTGCCCATG CCCCTGGAGG

AGGTGCTGCC TGACGTCTCT CCCCAGGCAT TGGATCTGCT GGGTCAATTC CTTCTCTACC
```

-continued
```
CTCCTCACCA GCGCATCGCA GCTTCCAAGG CTCTCCTCCA TCAGTACTTC TTCACAGCTC

CCCTGCCTGC CCATCCATCT GAGCTGCCGA TTCCTCAGCG TCTAGGGGGA CCTGCCCCCA

AGGCCCATCC AGGGCCCCCC CACATCCATG ACTTCCACGT GGACCGGCCT CTTGAGGAGT

CGCTGTTGAA CCCAGAGCTG ATTCGGCCCT TCATCCTGGA GGGGTGAGAA GTTGGCCCTG

GTCCCGTCTG CCTGCTCCTC AGGACCACTC AGTCCACCTG TTCCTCTGCC ACCTGCCTGG

CTTCACCCTC CAAGGCCTCC CCATGGCCAC AGTGGGCCCA CACCACACCC TGCCCCTTAG

CCCTTGCGAG GGTTGGTCTC GAGGCAGAGG TCATGTTCCC AGCCAAGAGT ATGAGAACAT

CCAGTCGAGC AGAGGAGATT CATGGCCTGT GCTCGGTGAG CCTTACCTTC TGTGTGCTAC

TGACGTACCC ATCAGGACAG TGAGCTCTGC TGCCAGTCAA GGCCTGCATA TGCAGAATGA

CGATGCCTGC CTTGGTGCTG CTTCCCCGAG TGCTGCCTCC TGGTCAAGGA GAAGTGCAGA

GAGTAAGGTG TCCTTATGTT GGAAACTCAA GTGGAAGGAA GATTTGGTTT GGTTTTATTC

TCAGAGCCAT TAAACACTAG TTCAGTATGT GAGATATAGA TTCTAAAAAC CTCAGGTGGC

TCTGCCTTAT GTCTGTTCCT CCTTCATTTC TCTCAAGGGA AATGGCTAAG GTGGCATTGT

CTCATGGCTC TCGTTTTTGG GGTCATGGGG AGGGTAGCAC CAGGCATAGC CACTTTTGCC

CTGAGGGACT CCTGTGTGCT TCACATCACT GAGCACTCAT TTAGAAGTGA GGGAGACAGA

AGTCTAGGCC CAGGGATGGC TCCAGTTGGG GATCCAGCAG GAGACCCTCT GCACATGAGG

CTGGTTTACC AACATCTACT CCCTCAGGAT GAGCGTGAGC CAGAAGCAGC TGTGTATTTA

AGGAAACAAG CGTTCCTGGA ATTAATTTAT AAATTTAATA AATCCCAATA TAATCCCAAA

AAAAAAAAAA AAAAAATTCC TGCGGCCGCA AGGA.
```

The present invention also relates to a substantially purified novel cyclin-dependent kinase which comprises a novel cyclin binding domain signature sequence (Pro-Asn-Gln-Ala-Leu-Arg-Glu; SEQ ID NO:1), lacks Thr14 and/or Tyr15 as well as the T-loop domain containing the conserved Thr160/161 residue. Any such nucleic acid may be isolated and characterized from a mammalian cell, including but not limited to human, human and rodent. A human form is an especially preferred form, such as the isolated cDNA exemplified herein as set forth in SEQ ID NO:2 and a dominant negative mutant form as set forth in SEQ ID NO:12.

The present invention also relates to biologically active fragments and/or mutants of a novel cyclin-dependent kinase which comprises the novel cyclin binding domain (Pro-Asn-Gln-Ala-Leu-Arg-Glu; SEQ ID NO:1), lacks Thr14 and/or Tyr15 which make up the conserved ATP binding motif of known CDKs, and also lacks the T-loop domain containing the conserved Thr160/161 residue, including but not necessarily limited to amino acid substitutions, deletions, additions, amino terminal truncations and carboxy-terminal truncations such that these mutations provide for proteins or protein fragments of diagnostic, therapeutic or prophylactic use. Any such nucleic acid may be isolated and characterized from a mammalian cell, including but not limited to human, human and rodent, with a human form being an especially preferred form.

A preferred aspect of the present invention is disclosed in SEQ ID NO:3 and FIG. 2, the amino acid sequence of CDK10. The open reading frame of the CDK10 coding region runs from nucleotide 210 to nucleotide 1182 of SEQ ID NO:2. The amino acid sequence of the novel cyclin-dependent kinase, CDK10, is disclosed herein as:

```
MDQYCILGRI GEGAHGIVFK AKHVETGEIV ALKKVALRRL EDGFPNQALR   (SEQ ID NO:3)

EIKALQEMED NQYVVQLKAV FPHGGGFVLA FEFMLSDLAE VVRHAQRPLA

QAQVKSYLQM LLKGVAFCHA NNIVHRDLKP ANLLISASGQ LKIADFGLAR

VFSPDGSRLY THQVATRSVG CIMGELLNGS PLFPGKNDIE QLCYVLRILG

TPNPQVWPEL TELPDYNKIS FKEQVPMPLE EVLPDVSPQA LDLLGQFLLY

PPHQRIAASK ALLHQYFFTA PLPAHPSELP IPQRLGGPAP KAHPGPPHIH

DFHVDRPLEE SLLNPELIRP FILEG.
```

Another preferred aspect of the present invention is disclosed in SEQ ID NO:11, wherein nucleotide 588 of the wild-type form (SEQ ID NO: 2) is mutated from "G" to "A".

Another preferred aspect of the present invention is the mutant protein, (CDK10-D127N), wherein nucleotide 588 of SEQ ID NO:11 is mutated from "G" to "A", as compared to the wild-type form (SEQ ID NO:2), which results in a change of Asp127 to Asn127 as compared to the wild-type amino acid sequence (SEQ ID NO:3), disclosed as SEQ ID NO:12.

The present invention also relates to methods of expressing the cyclin-dependent kinases disclosed herein, assays employing these cyclin-dependent kinases, cells expressing these cyclin-dependent kinases, and compounds identified through the use of these cyclin-dependent kinases, including modulators of the cyclin-dependents kinase either through direct contact with the cyclin-dependent kinase, an associated cyclin, or the CKD/cyclin complex. Such modulators identified in this process are useful as therapeutic agents for controlling cell growth or immune cell proliferation associated with human cancers. Additionally, an isolated and purified CDK10 cDNA which encodes CDK-10 or an active mutant thereof will also be useful for the recombinant production of large quantities of respective protein. The ability to produce large quantities of the protein would be useful for the production of a therapeutic agent comprising the CDK10 protein or a mutant such as the exemplified mutant disclosed herein. A therapeutic agent comprised of CDK10 protein would be useful in the treatment of cell cycle and/or CDK10 related diseases or conditions which are CDK10 responsive or possibly a therapeutic agent comprised of a mutant, including but not limited to CDK10-D127N, which may be useful in the treatment of cell cycle diseases or conditions which are responsive to the regulatory effects of the mutant kinase.

The isolated nucleic acid molecule of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

It is known that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide. Therefore, this invention is also directed to those DNA sequences which express RNA comprising alternative codons which code for the eventual translation of the identical amino acid, as shown below:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asp=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU Therefore, the present invention discloses codon redundancy which may result in differing DNA molecules expressing an identical protein. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate or a receptor for a ligand.

As used herein, a "biologically active equivalent" or "functional derivative" of a wild type CDK possesses a biological activity that is substantially similar to the biological activity of the wild type CDK10 protein. The term "functional derivative" is intended to include the "fragments," "mutants," "variants," "degenerate variants," "analogs" and "homologues" or to "chemical derivatives" of the wild type CDK10 protein. The term "fragment" is meant to refer to any polypeptide subset of wild type CDK10. The term "mutant" is meant to refer to a molecule that may be substantially similar to the wild type form but possesses distinguishing biological characteristics. Such altered characteristics include but are in no way limited to altered enzymatic activity, altered cyclin binding altered substrate binding, altered substrate affinity and altered sensitivity to chemical compounds affecting biological activity. An exemplified mutant is CDK10-D127N, wherein a single base mutation at nucleotide 588 of SEQ ID NO:2 results in a single amino acid substitution at residue 127, from aspartic acid to asparagine. This mutation alters kinase activity of CDK10-D127N as compared to the wild type CDK10 protein. The term "variant" is meant to refer to a molecule substantially similar in structure and function to either the entire wild type protein or to a fragment thereof A molecule is "substantially similar" to a wild type CDK10-like protein if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical.

The term "analog" refers to a molecule substantially similar in function to either the entire wild type CDK10-like protein or to a fragment thereof.

"Substantial homology" or "substantial similarity", when referring to nucleic acids means that the segments or their complementary strands, when optimally aligned and compared, are identical with appropriate nucleotide insertions or deletions, in at least 75% of the nucleotides. Alternatively, substantial homology exists when the segments will hybridize to a strand or its complement.

The term "substantial homology", when referring to polypeptides, indicates that the polypeptide or protein in question exhibits at least about 30% homology with the naturally occurring protein in question, usually at least about 65% homology.

The nucleic acids claimed herein may be present in whole cells or in cell lysates or in a partially purified or substantially purified form. A nucleic acid is considered substantially purified when it is purified away from environmental contaminants. Thus, a nucleic acid sequence isolated from cells is considered to be substantially purified when purified from cellular components by standard methods while a chemically synthesized nucleic acid sequence is considered to be substantially purified when purified from its chemical precursors.

Any of a variety of procedures may be used to clone CDK10. These methods include, but are not limited to, (1) a RACE PCR cloning technique (Frohman, et al., 1988, Proc. Natl. Acad. Sci.85: 8998–9002). 5' and/or 3' RACE may be performed to generate a full length cDNA sequence. This strategy involves using gene-specific oligonucleotide primers for PCR amplification of CDK10 cDNA. These gene-specific primers are designed through identification of an expressed sequence tag (EST) nucleotide sequence which has been identified by searching any number of publicly available nucleic acid and protein databases; (2) direct functional expression of the CDK10 cDNA following the construction of an CDK10-containing cDNA library in an appropriate expression vector system; (3) screening a CDK10-containing cDNA library constructed in a bacteriophage or plasmid shuttle vector with a labeled degenerate oligonucleotide probe designed from the amino acid sequence of the CDK10 protein; (4) screening a CDK10-containing cDNA library constructed in a bacteriophage or plasmid shuttle vector with a partial cDNA encoding the CDK10 protein. This partial cDNA is obtained by the specific PCR amplification of CDK10 DNA fragments through the design of degenerate oligonucleotide primers from the amino acid sequence known for other CDK kinases which are related to the CDK10 protein; (5) screening an CDK10-containing cDNA library constructed in a bacteriophage or plasmid shuttle vector with a partial cDNA encoding the CDK10 protein. This strategy may also involve using gene-specific oligonucleotide primers for PCR amplification of CDK10 cDNA identified as an EST as described above; or (6) designing 5' and 3' gene specific oligonucleotides using SEQ ID NO:2 as a template so that either the full length cDNA may be generated by known RACE techniques, or a portion of the coding region may be generated by these same known RACE techniques to generate and isolate a portion of the coding region to use as a probe to screen one of numerous types of cDNA and/or genomic libraries in order to isolate a full length version of the nucleotide sequence encoding CDK10.

It is readily apparent to those skilled in the art that other types of libraries, as well as libraries constructed from other cells types or species types, may be useful for isolating a CDK10-encoding DNA or a CDK10 homologue. Other types of libraries include, but are not limited to, cDNA libraries derived from other cells or cell lines other than human cells or tissue such as murine cells, rodent cells or any other such vertebrate host which may contain a CDK10-encoding DNA. Additionally a CDK10 gene may be isolated by oligonucleotide- or polynucleotide-based hybridization screening of a vertebrate genomic library, including but not limited to a human genomic library, a murine genomic library and a rodent genomic library, as well as concomitant human genomic DNA libraries.

It is readily apparent to those skilled in the art that suitable cDNA libraries may be prepared from cells or cell lines which have CDK10 activity. The selection of cells or cell lines for use in preparing a cDNA library to isolate a CDK10 cDNA may be done by first measuring cell associated CDK10 activity using any known assay for CDK activity.

Preparation of cDNA libraries can be performed by standard techniques well known in the art. Well known cDNA library construction techniques can be found for example, in Sambrook, et al., 1989, Molecular Cloning: A Laboratory Manual; Cold Spring Harbor Laboratory, Cold Spring Harbor, N.Y. Complementary DNA libraries may also be obtained from numerous commercial sources, including but not limited to Clontech Laboratories, Inc. and Stratagene.

It is also readily apparent to those skilled in the art that DNA encoding CDK10 may also be isolated from a suitable genomic DNA library. Construction of genomic DNA libraries can be performed by standard techniques well known in the art. Well known genomic DNA library construction techniques can be found in Sambrook, et al., supra.

In order to clone the CDK10 gene by one of the preferred methods, the amino acid sequence or DNA sequence of CDK10 or a homologous protein may be necessary. To accomplish this, the CDK10 or a homologous protein may be purified and partial amino acid sequence determined by automated sequenators. It is not necessary to determine the entire amino acid sequence, but the linear sequence of two regions of 6 to 8 amino acids can be determined for the PCR amplification of a partial CDK10 DNA fragment. Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the CDK10 sequence but others in the set will be capable of hybridizing to CDK10 DNA even in the presence of DNA oligonucleotides with mismatches. The mismatched DNA oligonucleotides may still sufficiently hybridize to the CDK10 DNA to permit identification and isolation of CDK10 encoding DNA. Alternatively, the nucleotide sequence of a region of an expressed sequence may be identified by searching one or more available genomic databases. Gene-specific primers may be used to perform PCR amplification of a cDNA of interest from either a cDNA library or a population of cDNAs. As noted above, the appropriate nucleotide sequence for use in a PCR-based method may be obtained from SEQ ID NO:2, either for the purpose of isolating overlapping 5' and 3' RACE products for generation of a full-length sequence coding for CDK10, or to isolate a portion of the nucleotide sequence coding for CDK10 for use as a probe to screen one or more cDNA- or genomic-based libraries to isolate a full-length sequence encoding CDK10 or CDK10-like proteins.

In an exemplified method, the RACE PCR technique (Frohman, et al., 1988, Proc. Natl. Acad. Sci 85: 8998–9002) is used for cloning a 5'coding region of CDK10 encoding DNA. First round PCR used adapter-ligated human placenta cDNA template (from Clontech), gene-specific primer PK22L234, (5'-TGATGCAGCCCACAGACCTG-3'; SEQ ID NO: 4) and an adapter primer AP1 (5'-

CCATCCTAATACGACTCACTATAGGGC-3'; SEQ ID NO:5). PCR amplification was performed using the Elongase™. Thermal cycling was completed and a portion of this first PCR reaction was added to a second PCR reaction as DNA template. This PCR reaction also differed from the first PCR reaction in that the nested gene specific primer PK22L161 (5'-GCCGTCTGGGGAAAAGA-3'; SEQ ID NO:6) and the nested adapter primer AP2 (5'-ACTCACTATAGGGCTCGAGCGGC-3', SEQ ID NO:7) were utilized.

An approximately 600 bp DNA product was identified from a 1% agarose electrophoresis gel, excised, and purified using a Qiagen PCR-spun column (Qiaquick™). This fragment was used directly for DNA sequencing using PK22L161 and AP2 primers, and for cloning into pCR2.1 using the Invitrogen TA-cloning kit.

A DNA fragment 3' to and overlapping the 600 bp 5' fragment was identified by searching public nucleic acid and protein databases. This 3' fragment is an approximately 1.8 Kb cDNA insert available as a NotI-HindIII fragment in a typical phagemid vector. This cDNA clone is readily identified by Genbank Accession No. H17727, Image Clone ID No. 50484, Washington University Clone ID No. ym40a06, and GBD Clone ID No. 423294. This cDNA was isolated from a library constructed from human infant brain mRNA. This construct is available from Research Genetics, Inc., 2130 Memorial Parkway SW, Hunstville, Ala. 35801 (http://www.resgen.com).

A full length CDK10 coding region was assembled in pLITMUS28 (New England Biolabs) as an expression cassette with a BamHI site appended just 5' to the ATG translational start codon. A BamHI-XbaI fragment bearing CDK10 was recloned into pcDNA3.1 expression vector (Invitrogen) and a BamHI-NcoI fragment bearing CDK10 was recloned into pBlueBacHis2 baculovirus expression vector (Invitrogen). A similar construct was generated which contains dominant-negative single base pair mutation of CDK10. This mutant was generated from pLITMUS28::CDK10 using the Stratagene "Quik Change" kit and primers 22U-D127N (5'-CAACATTGTACATCGGAACCTGAAA-CCTGCC-3'; SEQ ID NO: 8) and 22L-D127N (5'-GGCAGGTTTCAGGTTCC-GATGTACAATGTTG-3'; SEQ ID NO: 9). Both mutant constructions were subdloned into pcDNA3.1 (as a BamHI-XbaI fragment) and pBlueBacHis2 (as a BamHI-NcoI fragment), respectively.

The sequence for the 5' upstream sequences, coding region and 3' untranslated sequences for the human full-length cDNA encoding CDK10 is shown in SEQ ID NO:2. The deduced amino acid sequence of CDK10 from the cloned cDNA is shown in SEQ ID NO:3. Inspection of the determined cDNA sequence reveals the presence of a single open reading frame that encodes a 325 amino acid protein. The open reading frame of the CDK10 coding region runs from nucleotide 210 to nucleotide 1182 of SEQ ID NO:2.

The nucleotide sequence which encodes a preferred mutant form (Asp127 to Asn127), is disclosed as SEQ ID NO:11.

The amino acid sequence for this preferred mutant form, CDK10-D127N, is disclosed in SEQ ID NO:12.

A variety of mammalian expression vectors may be used to express recombinant CDK10 in mammalian cells. Expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

Commercially available mammalian expression vectors which may be suitable for recombinant CDK10 expression, include but are not limited to, pcDNA3.1 (Invitrogen), pBlueBacHis2 (Invitrogen), pLITMUS28, pLITMUS29, pLITMUS38 and pLITMUS39 (New England Bioloabs), pcDNAI, pcDNAIamp (Invitrogen), pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and λZD35 (ATCC 37565).

A variety of bacterial expression vectors may be used to express recombinant CDK10 in bacterial cells. Commercially available bacterial expression vectors which may be suitable for recombinant CDK10 expression include, but are not limited to pCR2.1 (Invitrogen), pET11a (Novagen), lambda gt11 (Invitrogen), pcDNAII (Invitrogen), pKK223-3 (Pharmacia).

A variety of fungal cell expression vectors may be used to express recombinant CDK10 in fungal cells. Commercially available fungal cell expression vectors which may be suitable for recombinant CDK10 expression include but are not limited to pYES2 (Invitrogen), Pichia expression vector (Invitrogen).

A variety of insect cell expression vectors may be used to express recombinant receptor in insect cells. Commercially available insect cell expression vectors which may be suitable for recombinant expression of CDK10 include but are not limited to pBlueBacIII and pBlueBacHis2 (Invitrogen).

The expression vector may be introduced into host cells via any one of a number of techniques including but not limited to transformation, transfection, lipofection, protoplast fusion, and electroporation. The expression vector-containing cells are clonally propagated and individually analyzed to determine whether they produce CDK10 protein. Identification of CDK10 expressing host cell clones may be done by several means, including but not limited to immunological reactivity with anti-CDK10 antibodies.

Expression of CDK10 DNA may also be performed using in vitro produced synthetic mRNA or native mRNA. Synthetic mRNA or mRNA isolated from CDK10 producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

An expression vector containing DNA encoding a CDK10-like protein may be used for expression of CDK10 in a recombinant host cell. Recombinant host cells may be prokaryotic or eukaryotic, including but not limited to bacteria such as E. coli, fingal cells such as yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, L cells L-M(TK$^-$) (ATCC CCL 1.3), L cells L-M (ATCC CCL 1.2), Saos-2 (ATCC HTB-85), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells via any one of a number of techniques including but not limited to transformation, transfection, protoplast fusion, and electroporation. The expression vector-containing cells are individually analyzed to determine whether they produce CDK10 protein. Identification of CDK10 expressing cells may be done by several means, including but not limited to immunological reactivity with anti-CDK10 antibodies, and the presence of host cell-associated CDK10 activity.

The cloned CDK10 cDNA obtained through the methods described above may be recombinantly expressed by molecular cloning into an expression vector (such as pcDNA3.1, pCR2.1, pBlueBacHis2 and pLITMUS28) containing a suitable promoter and other appropriate transcription regulatory elements, and transferred into prokaryotic or eukaryotic host cells to produce recombinant CDK10. Techniques for such manipulations can be found described in Sambrook, et al., supra, are discussed at length in the Example section and are well known and easily available to the artisan of ordinary skill in the art.

Expression of CDK10 DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the CDK10 cDNA sequence(s) that yields optimal levels of CDK10 protein, CDK10 cDNA molecules including but not limited to the following can be constructed: the full-length open reading frame of the CDK10 cDNA and various constructs containing portions of the cDNA encoding only specific domains of the protein or rearranged domains of the protein. All constructs can be designed to contain none, all or portions of the 5' and/or 3' untranslated region of CDK10. CDK10 activity and levels of protein expression can be determined following the introduction, both singly and in combination, of these constructs into appropriate host cells. Following determination of the CDK10 cDNA cassette yielding optimal expression in transient assays, this CDK10 cDNA construct is transferred to a variety of expression vectors (including recombinant viruses), including but not limited to those for mammalian cells, plant cells, insect cells, oocytes, bacteria, and yeast cells.

Levels of CDK10 protein in host cells is quantified by a variety of techniques including, but not limited to, immunoaffinity and/or ligand affinity techniques. CDK10-specific affinity beads or CDK10-specific antibodies are used to isolate $^{35}$S-methionine labeled or unlabelled CDK10 protein. Labeled CDK10 protein is analyzed by SDS-PAGE. Unlabelled CDK10 protein is detected by Western blotting, ELISA or RIA assays employing CDK10 specific antibodies.

Following expression of CDK10 in a host cell, CDK10 protein may be recovered to provide CDK10 in active form.

Several CDK10 purification procedures are available and suitable for use. Recombinant CDK10 may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography.

In addition, recombinant CDK10 can be separated from other cellular proteins by use of an immuno-affinity column made with monoclonal or polyclonal antibodies specific for full length CDK10, or polypeptide fragments of CDK10. Additionally, polyclonal or monoclonal antibodies may be raised against a synthetic peptide (usually from about 9 to about 25 amino acids in length) from a portion of the protein as disclosed in SEQ ID NO:3. Monospecific antibodies to CDK10 are purified from mammalian antisera containing antibodies reactive against CDK10 or are prepared as monoclonal antibodies reactive with CDK10 using the technique of Kohler and Milstein (1975, Nature 256: 495–497). Monospecific antibody as used herein is defined as a single antibody species or multiple antibody species with homogenous binding characteristics for CDK10. Homogenous binding as used herein refers to the ability of the antibody species to bind to a specific antigen or epitope, such as those associated with the CDK10, as described above. CDK10 specific antibodies are raised by immunizing animals such as mice, rats, guinea pigs, rabbits, goats, horses and the like, with an appropriate concentration of CDK10 or CDK10 synthetic peptide either with or without an immune adjuvant.

Preimmune serum is collected prior to the first immunization. Each animal receives between about 0.1 $\mu$g and about 1000 $\mu$g of CDK10 associated with an acceptable immune adjuvant. Such acceptable adjuvants include, but are not limited to, Freund's complete, Freund's incomplete, alum-precipitate, water in oil emulsion containing Corynebacterium parvum and tRNA. The initial immunization consists of the CDK10 protein or CDK10 synthetic peptide in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunizaiton. Those animals receiving booster injections are generally given an equal amount of CDK10 in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with CDK10 are prepared by immunizing inbred mice, preferably Balb/c, with CDK10. The mice are immunized by the IP or SC route with about 1 $\mu$g to about 100 $\mu$g, preferably about 10 $\mu$g, of CDK10 in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 $\mu$g of CDK10 in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using CDK10 as the antigen. The culture fluids are also tested in the Ouchterlony precipitation assay to determine the isotype of the mAb. Hybridoma cells from antibody positive wells are cloned by a technique such as the soft agar technique of MacPherson, 1973, Soft Agar Techniques, in *Tissue Culture Methods and Applications*, Kruse and Paterson, Eds., Academic Press.

Monoclonal antibodies are produced in vivo by injection of pristine primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of anti-CDK10 mAb is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of CDK10 in body fluids or tissue and cell extracts.

It is readily apparent to those skilled in the art that the above described methods for producing monospecific antibodies may be utilized to produce antibodies specific for CDK10 polypeptide fragments, or full-length CDK10 polypeptide.

CDK10 antibody affinity columns are made by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing CDK10 or CDK10 fragments are slowly passed through the column. The column is then washed with phosphate buffered saline until the optical density ($A_{280}$) falls to background, then the protein is eluted with 0.23 M glycine-HCl (pH 2.6). The purified CDK10 protein is then dialyzed against phosphate buffered saline.

The novel CDK10 of the present invention is suitable for use in an assay procedure for the identification of compounds which modulate CDK10 activity. Modulating CDK10 activity, as described herein includes the inhibition or activation of the protein and also includes directly or indirectly affecting the cell cycle regulatory properties associated with CDK10 activity. Compounds which modulate CDK10 activity include agonists, antagonists, inhibitors, activators, and compounds which directly or indirectly affect regulation of the CDK10 activity and/or the CDK10/cyclin association.

The CDK10 protein kinase of the present invention may be obtained from both native and recombinant sources for use in an assay procedure to identify CDK10 modulators. In general, an assay procedure to identify CDK10 modulators will contain the CDK10-protein of the present invention, native cyclin protein which will form a CDK10/cyclin complex, and a test compound or sample which contains a putative CDK10 modulator. The test compounds or samples may be tested directly on, for example, purified CDK10 protein whether native or recombinant, subcellular fractions of CDK10-producing cells whether native or recombinant, and/or whole cells expressing the CDK10 whether native or recombinant. The test compound or sample may be added to the CDK10 in the presence or absence of a known CDK10 modulator. The modulating activity of the test compound or sample may be determined by, for example, analyzing the ability of the test compound or sample to bind to CDK10 protein, activate the protein, inhibit CDK10 activity, inhibit or enhance the binding of other compounds to the CDK10 protein, modifying receptor regulation, or modifying an intracellular activity.

The identification of modulators of CDK10 activity are useful in treating disease states involving the cell cycle will be useful in controlling cell growth associated with cancer or immune cell proliferation. Other compounds may be useful for stimulating or inhibiting activity of the enzyme. These compounds could be of use in the treatment of diseases in which activation or inactivation of the CDK10 protein results in either cellular proliferation, cell death, nonproliferation, induction of cellular neoplastic transformations or metastatic tumor growth and hence could be used in the prevention and/or treatment of various cancers.

The present invention is also directed to methods for screening for compounds which modulate the expression of DNA or RNA encoding a CDK protein of the present invention or which modulates the function of a such a CDK protein. Compounds which modulate these activities may be DNA, RNA, peptides, proteins, or non-proteinaceous organic molecules. Compounds may modulate by increasing or attenuating the expression of DNA or RNA encoding the CDK protein, or the function of a CDK protein. Compounds that modulate the expression of DNA or RNA encoding the CDK protein or the biological function thereof may be detected by a variety of assays. The assay may be a simple "yes/no" assay to determine whether there is a change in expression or function. The assay may be made quantitative by comparing the expression or function of a test sample with the levels of expression or function in a standard sample. Kits containing modified CDK10, antibodies to CDK10, or modified CDK10 protein may be prepared by known methods for such uses.

The DNA molecules, RNA molecules, recombinant protein and antibodies of the present invention may be used to screen and measure levels of CDK10 DNA, RNA or protein. The recombinant proteins, DNA molecules, RNA molecules and antibodies lend themselves to the formulation of kits suitable for the detection and typing of CDK10. Such a kit would comprise a compartmentalized carrier suitable to hold in close confinement at least one container. The carrier would further comprise reagents such as recombinant CDK10 protein or anti-CDK10 antibodies suitable for detecting CDK10. The carrier may also contain a means for detection such as labeled antigen or enzyme substrates or the like.

Pharmaceutically useful compositions comprising modulators of CDK10 may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modified CDK10.

Therapeutic or diagnostic compositions of the invention are administered to an individual in amounts sufficient to treat or diagnose disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages. Alternatively, co-administration or sequential administration of other agents may be desirable.

The present invention also has the objective of providing suitable topical, oral, systemic and parenteral pharmaceutical formulations for use in the novel methods of treatment of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug Isolated and purified CDK10 is also be useful for the recombinant production of large quantities of CDK10 protein. The ability to produce large quantities of the protein would be useful for the production of a therapeutic agent comprising the CDK10 protein. A therapeutic agent comprised of CDK10 protein would be useful in the treatment of cell cycle and/or CDK10 related diseases or conditions which are CDK10 responsive.

By computer analysis of a genomic database, molecular cloning and DNA sequencing a novel member of the human CDK gene family has been identified. This new cDNA fragment encodes a novel cyclin-dependent kinase which comprises a novel cyclin binding domain signature sequence, lacks Thr14 and/or Tyr15 within the conserved ATP binding motif of known CDKs, and also lacks the T-loop domain containing the conserved Thr160/161 residue.

Northern hybridization experiments with RNA from various cell and tissues indicates that CDK10 is expressed in various human tissue, including brain, testis, pituitary gland and adrenal gland derived cells or tissues.

The following examples are provided as illustrative of the present invention without, however, limiting the same thereto.

EXAMPLE 1

Isolation and Characterization of DNA Fragments Encoding CDK

A 3' portion of the CDK10 coding region was detected among the Merck-Washington University EST's as 5' EST H17727. EST "H17727" resembled several CDK and MAPK genes. The pH17727 plasmid construct comprising the 3' coding region and 3' untranslated region of CDK10 is contained within a NotI-HindIII fragment of approximately 1.8 Kb, in a typical phagemid vector. The 5' portion of this fragment overlaps the 3' end of the 600 bp. This cDNA clone is publicly available by Genbank Accession No. H17727, Image Clone ID No. 50484, Washington University Clone ID No. ym40a06, and GBD Clone ID No. 423294. This cDNA was isolated from a library constructed from human infant brain mRNA. This construct is available from Research Genetics, Inc., 2130 Memorial Parkway SW, Hunstville, Ala. 35801 (http://www. resgen.com).

The 5' portion of the gene was isolated by performing 5' RACE (Frohman., et al., 1988, *Proc. Natl. Acad. Sci.* 85: 8998–9002) using Marathon™-ready human placenta cDNA available from Clontech (Protocol #PT1156-1, Catalog #K1802-1). Adapter-ligated double stranded cDNA generated from human placenta mRNA was used as a template for PCR amplification using a gene specific primer PK22L234 (5'-TGATGCAGCCCACAGACCTG-3'; SEQ ID NO: 4) and an adapter primer AP1 (5'-CCATCCTAATACGACTCACTATAGGGC-3' SEQ ID NO:5). PCR amplification was performed using the ElongaseTM long-PCR enzyme mix (stored in 20 mM Tris-HCl (pH 8.0 at 25° C.), 0.1 mM EDTA, 1 mM DTT, stabilizers and 50% (v/v) glycerol) and PCR reaction buffer obtained from Gibco-BRL. The buffer comprised 300 mM Tris-SO$_4$ (pH 9.1 at 25° C.), 90 mM (NH$_4$)$_2$SO$_4$ and 1.5 mM MgSO$_4$. Two microliters of Marathon placenta cDNA template and 10 pmoles each of PK22L234 and AP1 were added to the reaction mix and brought to a total volume of 20 ml with sterile water. Thermal cycling was (1) 94° C./30 sec, 68° C./6 min for 5 cycles; (2) 94° C./30 sec, 64° C./30 sec, 68° C./4 min for 5 cycles; an 94° C./30 sec, 62° C./30 sec and 68° C./4 min for 30 cycles. One microliter from a 1/20 dilution of this first PCR reaction was added to a second PCR reaction as DNA template. This PCR reaction also differed from the first PCR reaction in that nested primers PK22L161 (5'-GCCGTCTGGGGAAAAGA-3'; SEQ ID NO:6) and AP2 (5'-ACTCACTATAGGGCTCGAGCGGC-3', SEQ ID NO:7) were used. An approximately 600 bp PCR product was identified from a 1% agarose electrophoresis gel, excised, and purified using a Qiagen PCR-spun column. This fragment was used directly for DNA sequencing using PK22L161 and AP2 oligonucleotide primers.

The Marathon™-ready human placenta cDNA available from Clontech is enhanced by ligation of a double-stranded, 5' overhang adapter to the double stranded cDNA template. The 3' end of the adapter is blocked by an amine group to prevent extension during PCR amplification. It is within the non-extended 3' region that the AP1 oligo will hybridize. Therefore, AP1 does not hybridize and extend any of the original cDNA template molecules, instead beginning extension and amplification in the second round of PCR.

EXAMPLE 2
Construction of a Full Length DNA Fragment Encoding CDK10

The 3' portion of a DNA fragment which encodes CDK10 is contained within a DNA plasmid vector, pH17727. This insert contains a 5' XhoI site unique to the insert and a NcoI site in the 3' unstranslated region unique to the insert. This XhoI-NcoI fragment was isolated and subcloned into XhoI-NcoI digested pLITMUS28 plasmid DNA (New England Biolabs), resulting in pLITMUS28:H17727.

The 600 bp PCR fragments obtained from 5' RACE were cloned into pCR2.1 (Invitrogen) using the Invitrogen TA-cloning kit as described by the manufacturer. A PmlI restriction site is located at approximately the midpoint of the 600 bp PCR product. The PmlI site was used to construct a wild type form of the 600 bp 5' fragment from 2 independent 5' RACE PCR clones, pPK22bo4 and pPK22do4. The PmlI-BamHI restriction fragment of pPK22bo4 (which contains a mutation 3' to the PmlI site) was replaced with the with the PmlI-BamHI fragment of clone pPK22do4 (which contains a mutation 5' to the PmlI site). The resulting clone, pPK22bo4/do4, overlaps the 5' portion of pH17727 through the unique XhoI restriction site. An SpeI-BamHI-NdeI restriction site cluster was appended just 5' to the ATG translational start codon by PCR-amplisying the insert from clone pPK(22bo4/do4 using primers PK(22L661 (5'-GCCGTCTGGGGAAAAGA-3'; SEQ ID NO: 6) and PK(22U210 (5'-GGACTAGTGGATCCATATGGACCAGT-ACTGCATCCT-3'; SEQ ID NO:10). The resulting PCR fragment was digested with Spe1 and XhoI and ligated into BamHI-XhoI digested pLITMUS28:H17727, resulting in pLITMUS28:CDK10 (FIG. 3).

EXAMPLE 3
Construction of CDK10 Mammalian Expression Vector

A BamHI-XbaI fragment from pLITMUS28:CDK10 comprising the CKD10 coding region was subcloned into the mammalian expression vector, pcDNA3.1 (Invitrogen), which was previously digested with BamHI and XbaI. The resulting construct, pcDNA3.1:CDK10, contains a portion of the CMV promoter and a T7 primer site upstream of the CDK10 ATG translational start codon as well as the BGH polyA region downstream of the translational termination codon. Of course, other components to allow growth in *E. coli* and mammalian cells are present in this vector.

EXAMPLE 4
Construction of CDK10 Baculovirus Transfer Vector

A BamHI-NcoI fragment from pLITMUS28:CDK10 containing the CKD10 coding region was cloned into the baculovirus expression vector, pBlueBacHis2 (Invitrogen), which was previously digested with BamHI and NcoI. The resulting construct, pBBH:CDK10, may be used to express recombinant CDK10 from insect cells by following the manufacturer's instructions (e.g., see Invitrogen Cat. No. V375-20 for pBlueBacHis2 A, B, and C).

EXAMPLE 5
Construction of DNA Fragment Encoding a CDK10 Dominant-Negative Mutant The pLITMUS:CDK10 construct (see Example 2) was mutated to generate a "dominant-negative" single base pair mutation. This mutation was generated from pLITMUS28:CDK10 using the Stratagene "Quik Change" kit and primers 22U-D127N: (5'-CAAC-ATTGTACATCGGAACCTGAAACCTGCC-3'; SEQ ID NO:8), and 22L-D127N: (5'-GGCAGGTTTCA-GGTTCCGATGTACAATGTTG-3'; SEQ ID NO: 9), according to the manufacturer's instructions. The dominant-negative mutation changes the codon GAC (at nucleotides 588–590 of SEQ ID NO:2) to AAC (at nucleotides 588–590 of SEQ ID NO:11), thus deletion essential amino acid Asp127 to Asn127 (see SEQ ID NO:12), which inactivates kinase activity (see Example 7 and van den Heuvel & Harlow, 1993, *Science* 262:2050–2054). A CDK10-D127N construction was subcloned into pcDNA3.1 (as a BamHI-Xba1 fragment), resulting in pcDNA3.1:CDK10-d127N. A CDK10-D127N construction was also subcloned into pBlueBacHis2 (as a BamHI-Nco1 fragment), resulting in pBBH:CDK10-d127N.

EXAMPLE 6
Tissue Distribution of CDK10 Expression

Human multiple tissue Northern Blot #7760-1, Human Brain Northern Blot II #7755-1, Human Brain Northern Blot III #7750-1, and "Human multiple tissue Northern Dot Blot were purchased from Clontech. The probe was made by PCR amplifying the NotI-HindIII insert from pH17727 using the "Universal"(5'-CCCAGTCACGACGTTGT-AAAACG-3'; SEQ ID NO:13) and "Reverse" (5'-AGCGGATAACAATTTCACACAGG-3': SEQ ID NO:14) primers from Gibco BRL. Twenty-five ng of the probe was labeled with $^{32}$P using a Pharmacia "Ready-to-go" random priming kit and hybridized to the four Northern blots at high stringency according to Clontech instructions.

Figure 4:
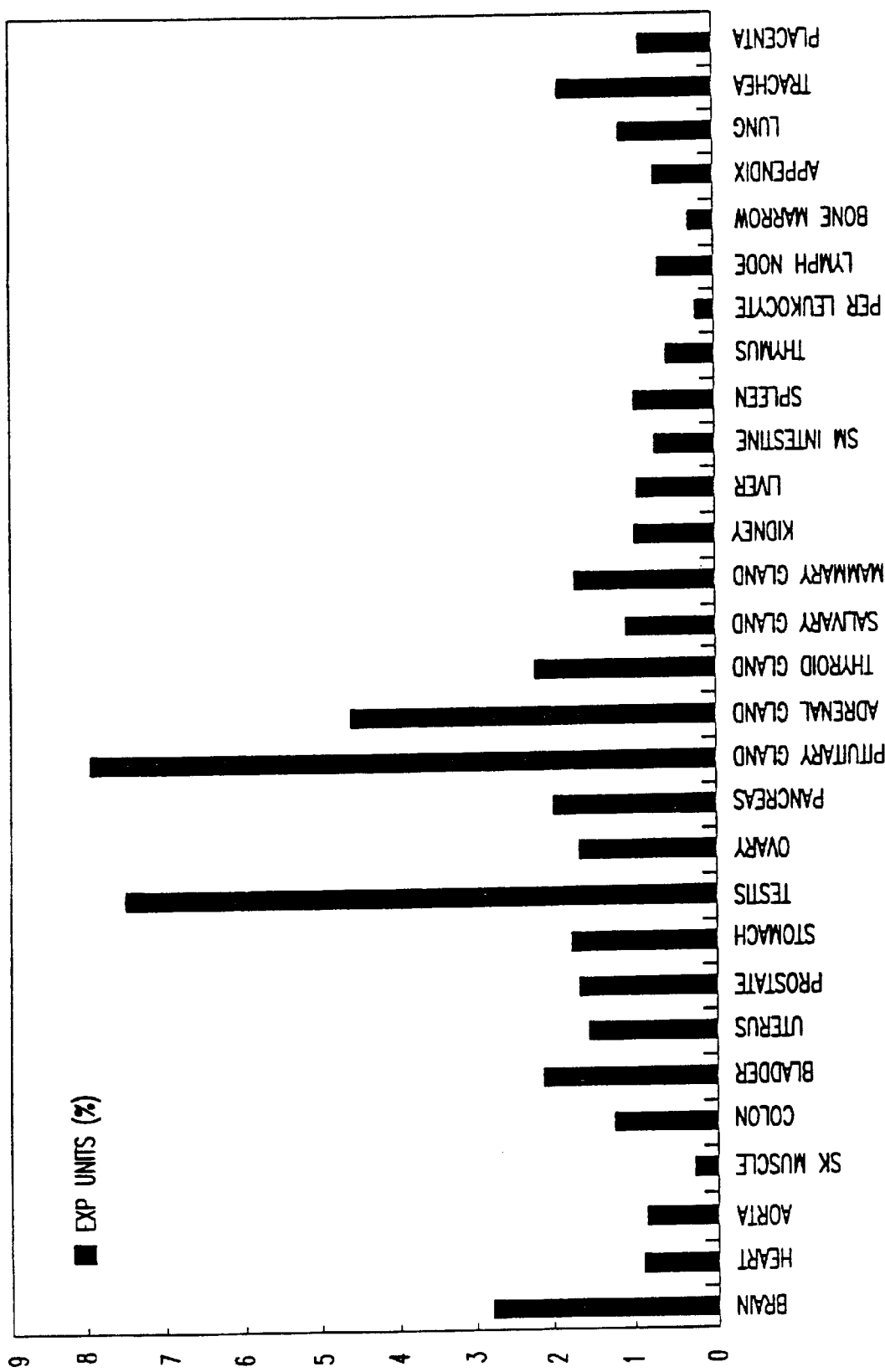
FIG. 4 shows northern blot an analysis of human tissue mRNA hybridized to a $^{32}$P-labeled probe from the 3' region of the DNA fragment encoding human CDK10.
Figure 5:
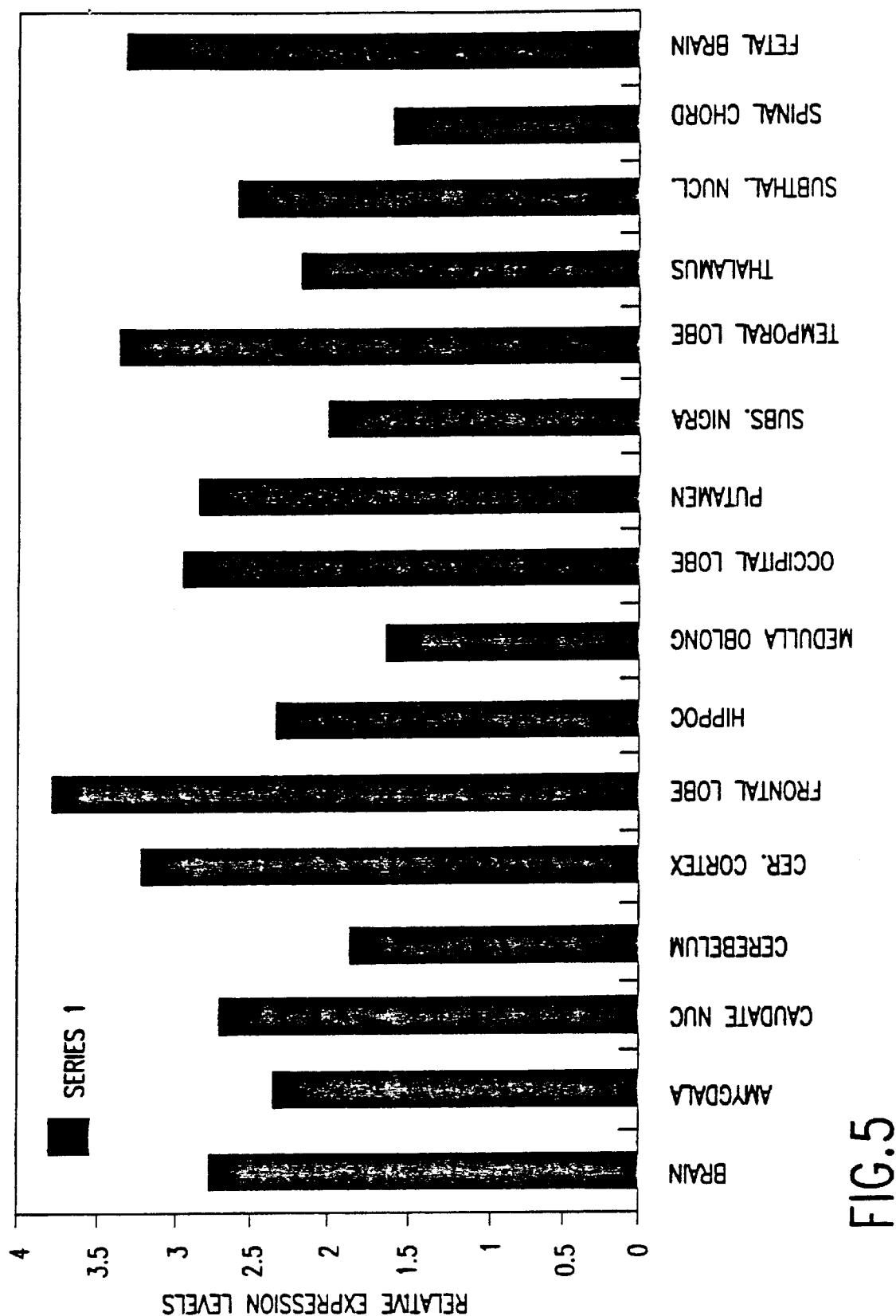
FIG. 5 shows northern blot analysis of human tissue mRNA hybridized to a $^{32}$P-labeled probe from the 3' region of the DNA fragment encoding human CDK10.

FIG. 4 and FIG. 5 show Northern data indicating the presence of CDK10 transcripts in a variety of adult human tissue (FIG. 4) as well as in specific regions of the adult and fetal human brain (FIG. 5). This data shows increased expression levels in the testis as well as in pituitary and adrenal glands. Expression in various regions of the brain was relatively constant, with increased expression seen in the frontal and temporal lobes and the cerebral cortex.

EXAMPLE 7
Effect of CDK:D127N on Cell Growth

Human osteosarcoma cell line Saos2 (ATCC HBT-85) was grown in DMEM high glucose medium+glutamine+

10% fetal calf serum (in concentrations as recommended by Gibco-BRL). Two replicates of the experiment were performed sequentially. Cells were split 1:6 into 10 cm culture dishes two days prior to transfection. Transfection was performed using the CaPO4 method according to Chen and Okayama (1987, *Mol. and Cell. Biol.* 7: 2745–2752). Ten ug of each plasmid DNA (pcDNA3.1, pcDNA3:CDK10, pcDNA3:CDK10-D127N) was transfected into ~60% confluent cells in each 10 cm dish. Cells were rinsed 2× with Dulbecco's PBS (Gibco-BRL) and 10 mL fresh medium was added. After two days, cells were trypsinized and plated in 12 well dishes in fresh medium+500 ug/mL geneticin (Gibco-BRL). At 11 and 16 days after plating, colony counts were made to determine how many transfected cells were capable of growth and colony formation (Table 1). This data indicates that expression of the kinase inactive "dominant-negative" form of CDK10 (i.e., CDK10-D127N) impairs colony formation by analogy to the data presented in van den Heuvel and Harlow (1993, *Science* 262: 2050–2054).

TABLE 1

| DNA construct | Day 11 (Colonies) | | Day 16 (# Colonies) | |
|---|---|---|---|---|
| | Rep A | Rep B | Rep A | Rep B |
| no DNA | 2 | 1 | 0 | 0 |
| pcDNA3.1 | 23 | 42 | 16 | 40 |
| pcDNA3.1:CDK10 | 32 | 59 | 23 | 49 |
| pcDNA3.1:CDK-D127N | 5 | 1 | 2 | 1 |

EXAMPLE 8

Specific Effect of the Dominant Mutant CDK:D127N on Expression of Cell Cycle Genes HeLa cervical carcinoma cells were treated for 48 hours with a control adenovirus deleted for the E1 and E3 genes or the same adenovirus which comprised the construct encoding CDK10-D127N. Western blots were performed with a rabbit antibody raised to the C-terminal 25 amino acids of the CDK10 protein (amino acid 301–amino acid 325 of SEQ ID NO: 3). The cell line transfected with Ad/CDK10-D127N expressed CDK10-D127N at a 50-fold higher level than endogenous, wild type CDK10. The two infected cell populations were subjected to mRNA isolations and probes were prepared for gene expression DNA chip studies essentially as described by Lockhart, et al. (1996, *Nature Biotechnology* 14:1675–1680). Among the genes which were suppressed at the mRNA level by CDK10-D127N are summarized in Table 2.

TABLE 2

| GENE | Ad/CDK10-D127N | Ad- Control |
|---|---|---|
| CDC25b | 8.3 | 19.1 |
| CDK7 | 3.1 | 8.5 |
| CKS1 | 26.3 | 82.5 |
| CKS2 | 11.6 | 98.3 |
| Cyclin B | 16.5 | 41.5 |
| Cyclin D1 | 4.5 | 11.5 |
| poly-Ubiquitin | 186.5 | 664.5 |

1 Quantified arbitrary expression units measured from the fluorescence image of the oligonucleotide array.

These data indicate a cell cycle block by the dominant-negative mutant gene, CDK10-D127N, which shows the importance of the CDK10 protein to the cell cycle. Cell cycle analysis (using a fluorescence-activated cell sorter, or FACS) of cells treated for 48 hours with the two viruses indicate that cells are not blocked in any particular phase of the cell cycle.

The data reported in the above Example sections show the importance of CDK10 in the cell cycle. Therefore, a therapeutic agent comprising the CDK10 protein would be useful in the treatment of cell cycle and/or CDK10 related diseases or conditions which are CDK10 responsive as well as showing a potential use for a dominant-negative mutant such as CDK10-D127N, which may be useful in the treatment of cell cycle diseases or conditions which are responsive to the mtuant proteins ability to regulate a phase or phases of the cell cycle.

What is claimed is:

1. A purified human cyclin dependent kinase protein which comprises the amino acid sequence as set forth in SEQ ID NO:3.

2. A purified human cyclin dependent kinase protein which consists of the amino acid sequence as set forth in SEQ ID NO:3.

3. A purified human cyclin dependent kinase protein which comprises the amino acid sequence as set forth in SEQ ID NO:12.

4. A purified human cyclin dependent kinase protein which consists of the amino acid sequence as set forth in SEQ ID NO:12.

5. A method for determining whether a substance is capable of binding to cyclin dependent kinase 10 protein comprising:

(a) providing test cells by transfecting cells with an expression vector that directs the expression of a cyclin dependent kinase 10 protein in the cells, wherein said cyclin dependent kinase 10 protein comprises an amnino acid sequence as set forth in SEQ ID NO:3;

(b) exposing the test cells to the substance;

(c) measuring the amount of binding of the substance to said cyclin dependent kinase 10 protein;

(d) comparing the amount of binding of the substance to said cyclin dependent kinase 10 protein in the test cells with the amount of binding of the substance to control cells that have not been transfected with said cyclin dependent kinase 10 protein.

6. A method for determining whether a substance is capable of binding to cyclin dependent kinase 10 protein comprising:

(a) providing test cells by transfecting cells with an expression vector that directs the expression of a cyclin dependent kinase 10 protein in the cells, wherein said cyclin dependent kinase 10 protein comprises an amino acid sequence as set forth in SEQ ID NO:12;

(b) exposing the test cells to the substance;

(c) measuring the amount of binding of the substance to said cyclin dependent kinase 10 protein;

(d) comparing the amount of binding of the substance to said cyclin dependent kinase 10 protein in the test cells with the amount of binding of the substance to control cells that have not been transfected with said cyclin dependent kinase 10 protein.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Pro Asn Gln Ala Leu Arg Glu
1            5

(2) INFORMATION FOR SEQ ID NO:2:

(i) SEQUENCE CHARACTERISTICS:
      (A) LENGTH: 2074 base pairs (B) TYPE: nucleic acid
(C) STRANDEDNESS: double
(D) TOPOLOGY: both (ii) MOLECULE TYPE: cDNA (xi) SEQUENCE DESCRIPTION: SEQ ID NO:2:

```
GAAAAGGCGC AGTGGGGCCC GGAGCTGTCA CCCCTGACTC GACGCAGCTT CCGTTCTCCT    60
GGTGACGTCG CCTACAGGAA CCGCCCCAGT GGTCAGCTGC CGCGCTGTTG CTAGGCAACA   120
GCGTGCGAGC TCAGATCAGC GTGGGGTGGA GGAGAAGTGG AGTTTGGAAG TTCAGGGGCA   180
CAGGGGCACA GGCCCACGAC TGCAGCGGGA TGGACCAGTA CTGCATCCTG GGCCGCATCG   240
GGGAGGGCGC CCACGGCATC GTCTTCAAGG CCAAGCACGT GGAGACTGGC GAGATAGTTG   300
CCCTCAAGAA GGTGGCCCTA AGGCGGTTGG AAGACGGCTT CCCTAACCAG GCCCTGCGGG   360
AGATTAAGGC TCTGCAGGAG ATGGAGGACA ATCAGTATGT GGTACAACTG AAGGCTGTGT   420
TCCCACACGG TGGAGGCTTT GTGCTGGCCT TTGAGTTCAT GCTGTCGGAT CTGGCCGAGG   480
TGGTGCGCCA TGCCCAGAGG CCACTAGCCC AGGCACAGGT CAAGAGCTAC CTGCAGATGC   540
TGCTCAAGGG TGTCGCCTTC TGCCATGCCA ACAACATTGT ACATCGGGAC CTGAAACCTG   600
CCAACCTGCT CATCAGCGCC TCAGGCCAGC TCAAGATAGC GGACTTTGGC CTGGCTCGAG   660
TCTTTTCCCC AGACGGCAGC CGCCTCTACA CACACCAGGT GGCCACCAGG TCTGTGGGCT   720
GCATCATGGG GGAGCTGTTG AATGGGTCCC CCCTTTTCCC GGGCAAGAAC GATATTGAAC   780
AGCTTTGCTA TGTGCTTCGC ATCTTGGGCA CCCCAAACCC TCAAGTCTGG CCGGAGCTCA   840
CTGAGCTGCC GGACTACAAC AAGATCTCCT TTAAGGAGCA GGTGCCCATG CCCCTGGAGG   900
AGGTGCTGCC TGACGTCTCT CCCCAGGCAT TGGATCTGCT GGGTCAATTC CTTCTCTACC   960
CTCCTCACCA GCGCATCGCA GCTTCCAAGG CTCTCCTCCA TCAGTACTTC TTCACAGCTC  1020
CCCTGCCTGC CCATCCATCT GAGCTGCCGA TTCCTCAGCG TCTAGGGGGA CCTGCCCCCA  1080
AGGCCCATCC AGGGCCCCCC CACATCCATG ACTTCCACGT GGACCGGCCT CTTGAGGAGT  1140
CGCTGTTGAA CCCAGAGCTG ATTCGGCCCT TCATCCTGGA GGGGTGAGAA GTTGGCCCTG  1200
GTCCCGTCTG CCTGCTCCTC AGGACCACTC AGTCCACCTG TTCCTCTGCC ACCTGCCTGG  1260
CTTCACCCTC CAAGGCCTCC CCATGGCCAC AGTGGGCCCA CACCACACCC TGCCCCTTAG  1320
CCCTTGCGAG GGTTGGTCTC GAGGCAGAGG TCATGTTCCC AGCCAAGAGT ATGAGAACAT  1380
CCAGTCGAGC AGAGGAGATT CATGGCCTGT GCTCGGTGAG CCTTACCTTC TGTGTGCTAC  1440
TGACGTACCC ATCAGGACAG TGAGCTCTGC TGCCAGTCAA GGCCTGCATA TGCAGAATGA  1500
CGATGCCTGC CTTGGTGCTG CTTCCCCGAG TGCTGCCTCC TGGTCAAGGA GAAGTGCAGA  1560
GAGTAAGGTG TCCTTATGTT GGAAACTCAA GTGGAAGGAA GATTTGGTTT GGTTTTATTC  1620
TCAGAGCCAT TAAACACTAG TTCAGTATGT GAGATATAGA TTCTAAAAAC CTCAGGTGGC  1680
TCTGCCTTAT GTCTGTTCCT CCTTCATTTC TCTCAAGGGA AATGGCTAAG GTGGCATTGT  1740
CTCATGGCTC TCGTTTTTGG GGTCATGGGG AGGGTAGCAC CAGGCATAGC CACTTTTGCC  1800
CTGAGGGACT CCTGTGTGCT TCACATCACT GAGCACTCAT TTAGAAGTGA GGGAGACAGA  1860
AGTCTAGGCC CAGGGATGGC TCCAGTTGGG GATCCAGCAG GAGACCCTCT GCACATGAGG  1920
CTGGTTTACC AACATCTACT CCCTCAGGAT GAGCGTGAGC CAGAAGCAGC TGTGTATTTA  1980
AGGAAACAAG CGTTCCTGGA ATTAATTTAT AAATTTAATA AATCCCAATA TAATCCCAAA  2040
AAAAAAAAAA AAAAAATTCC TGCGGCCGCA AGGA                              2074
```

(2) INFORMATION FOR SEQ ID NO:3:

(i) SEQUENCE CHARACTERISTICS:
        (A) LENGTH: 325 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Asp Gln Tyr Cys Ile Leu Gly Arg Ile Gly Glu Gly Ala His Gly
1               5                   10                  15

Ile Val Phe Lys Ala Lys His Val Glu Thr Gly Glu Ile Val Ala Leu
            20                  25                  30

Lys Lys Val Ala Leu Arg Arg Leu Glu Asp Gly Phe Pro Asn Gln Ala
        35                  40                  45

Leu Arg Glu Ile Lys Ala Leu Gln Glu Met Glu Asp Asn Gln Tyr Val
    50                  55                  60

Val Gln Leu Lys Ala Val Phe Pro His Gly Gly Phe Val Leu Ala
65                  70                  75                  80

Phe Glu Phe Met Leu Ser Asp Leu Ala Glu Val Val Arg His Ala Gln
                85                  90                  95

Arg Pro Leu Ala Gln Ala Gln Val Lys Ser Tyr Leu Gln Met Leu Leu
            100                 105                 110

Lys Gly Val Ala Phe Cys His Ala Asn Asn Ile Val His Arg Asp Leu
        115                 120                 125

Lys Pro Ala Asn Leu Leu Ile Ser Ala Ser Gly Gln Leu Lys Ile Ala
    130                 135                 140

Asp Phe Gly Leu Ala Arg Val Phe Ser Pro Asp Gly Ser Arg Leu Tyr
145                 150                 155                 160

Thr His Gln Val Ala Thr Arg Ser Val Gly Cys Ile Met Gly Glu Leu
                165                 170                 175

Leu Asn Gly Ser Pro Leu Phe Pro Gly Lys Asn Asp Ile Glu Gln Leu
            180                 185                 190

Cys Tyr Val Leu Arg Ile Leu Gly Thr Pro Asn Pro Gln Val Trp Pro
        195                 200                 205

Glu Leu Thr Glu Leu Pro Asp Tyr Asn Lys Ile Ser Phe Lys Glu Gln
    210                 215                 220

Val Pro Met Pro Leu Glu Glu Val Leu Pro Asp Val Ser Pro Gln Ala
225                 230                 235                 240

Leu Asp Leu Leu Gly Gln Phe Leu Leu Tyr Pro Pro His Gln Arg Ile
                245                 250                 255

Ala Ala Ser Lys Ala Leu Leu His Gln Tyr Phe Thr Ala Pro Leu
            260                 265                 270

Pro Ala His Pro Ser Glu Leu Pro Ile Pro Gln Arg Leu Gly Gly Pro
        275                 280                 285

Ala Pro Lys Ala His Pro Gly Pro Pro His Ile His Asp Phe His Val
    290                 295                 300

Asp Arg Pro Leu Glu Glu Ser Leu Leu Asn Pro Glu Leu Ile Arg Pro
305                 310                 315                 320

Phe Ile Leu Glu Gly
                325
```

(2) INFORMATION FOR SEQ ID NO:4:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:4:

TGATGCAGCC CACAGACCTG                                       20

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:5:

CCATCCTAAT ACGACTCACT ATAGGGC                               27

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:6:

GCCGTCTGGG GAAAAGA                                          17

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:7:

ACTCACTATA GGGCTCGAGC GGC                                   23

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:8:

CAACATTGTA CATCGGAACC TGAAACCTGC C                          31

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:9:

GGCAGGTTTC AGGTTCCGAT GTACAATGTT G                                    31

(2) INFORMATION FOR SEQ ID NO:10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:10:

GGACTAGTGG ATCCATATGG ACCAGTACTG CATCCT                               36

(2) INFORMATION FOR SEQ ID NO:11:

(i) SEQUENCE CHARACTERISTICS:
        (A) LENGTH: 2074 base pairs
        (B) TYPE: nucleic acid
        (C) STRANDEDNESS: single
        (D) TOPOLOGY: both (ii) MOLECULE TYPE: cDNA (xi) SEQUENCE DESCRIPTION: SEQ ID NO:11:

GAAAAGGCGC AGTGGGGCCC GGAGCTGTCA CCCCTGACTC GACGCAGCTT CCGTTCTCCT     60

GGTGACGTCG CCTACAGGAA CCGCCCCAGT GGTCAGCTGC CGCGCTGTTG CTAGGCAACA    120

GCGTGCGAGC TCAGATCAGC GTGGGTGGA GGAGAAGTGG AGTTTGGAAG TTCAGGGGCA    180

CAGGGGCACA GGCCCACGAC TGCAGCGGGA TGGACCAGTA CTGCATCCTG GCCGCATCG    240

GGGAGGGCGC CCACGGCATC GTCTTCAAGG CCAAGCACGT GGAGACTGGC GAGATAGTTG    300

CCCTCAAGAA GGTGGCCCTA AGGCGGTTGG AAGACGGCTT CCCTAACCAG GCCCTGCGGG    360

AGATTAAGGC TCTGCAGGAG ATGGAGGACA ATCAGTATGT GGTACAACTG AAGGCTGTGT    420

TCCCACACGG TGGAGGCTTT GTGCTGGCCT TTGAGTTCAT GCTGTCGGAT CTGGCCGAGG    480

TGGTGCGCCA TGCCCAGAGG CCACTAGCCC AGGCACAGGT CAAGAGCTAC CTGCAGATGC    540

TGCTCAAGGG TGTCGCCTTC TGCCATGCCA ACAACATTGT ACATCGGAAC CTGAAACCTG    600

CCAACCTGCT CATCAGCGCC TCAGGCCAGC TCAAGATAGC GGACTTTGGC CTGGCTCGAG    660

TCTTTTCCCC AGACGGCAGC CGCCTCTACA CACACCAGGT GGCCACCAGG TCTGTGGGCT    720

GCATCATGGG GGAGCTGTTG AATGGGTCCC CCTTTTCCC GGGCAAGAAC GATATTGAAC    780

AGCTTTGCTA TGTGCTTCGC ATCTTGGGCA CCCCAAACCC TCAAGTCTGG CCGGAGCTCA    840

CTGAGCTGCC GGACTACAAC AAGATCTCCT TTAAGGAGCA GGTGCCCATG CCCCTGGAGG    900

AGGTGCTGCC TGACGTCTCT CCCCAGGCAT TGGATCTGCT GGGTCAATTC CTTCTCTACC    960

CTCCTCACCA GCGCATCGCA GCTTCCAAGG CTCTCCTCCA TCAGTACTTC TTCACAGCTC   1020

CCCTGCCTGC CCATCCATCT GAGCTGCCGA TTCCTCAGCG TCTAGGGGGA CCTGCCCCCA   1080

AGGCCCATCC AGGGCCCCCC CACATCCATG ACTTCCACGT GGACCGGCCT CTTGAGGAGT   1140

-continued

```
CGCTGTTGAA CCCAGAGCTG ATTCGGCCCT TCATCCTGGA GGGGTGAGAA GTTGGCCCTG     1200

GTCCCGTCTG CCTGCTCCTC AGGACCACTC AGTCCACCTG TTCCTCTGCC ACCTGCCTGG     1260

CTTCACCCTC CAAGGCCTCC CCATGGCCAC AGTGGGCCCA CACCACACCC TGCCCCTTAG     1320

CCCTTGCGAG GGTTGGTCTC GAGGCAGAGG TCATGTTCCC AGCCAAGAGT ATGAGAACAT     1380

CCAGTCGAGC AGAGGAGATT CATGGCCTGT GCTCGGTGAG CCTTACCTTC TGTGTGCTAC     1440

TGACGTACCC ATCAGGACAG TGAGCTCTGC TGCCAGTCAA GGCCTGCATA TGCAGAATGA     1500

CGATGCCTGC CTTGGTGCTG CTTCCCCGAG TGCTGCCTCC TGGTCAAGGA GAAGTGCAGA     1560

GAGTAAGGTG TCCTTATGTT GGAAACTCAA GTGGAAGGAA GATTTGGTTT GGTTTTATTC     1620

TCAGAGCCAT TAAACACTAG TTCAGTATGT GAGATATAGA TTCTAAAAAC CTCAGGTGGC     1680

TCTGCCTTAT GTCTGTTCCT CCTTCATTTC TCTCAAGGGA AATGGCTAAG GTGGCATTGT     1740

CTCATGGCTC TCGTTTTTGG GGTCATGGGG AGGGTAGCAC CAGGCATAGC CACTTTTGCC     1800

CTGAGGGACT CCTGTGTGCT TCACATCACT GAGCACTCAT TTAGAAGTGA GGGAGACAGA     1860

AGTCTAGGCC CAGGGATGGC TCCAGTTGGG GATCCAGCAG GAGACCCTCT GCACATGAGG     1920

CTGGTTTACC AACATCTACT CCCTCAGGAT GAGCGTGAGC CAGAAGCAGC TGTGTATTTA     1980

AGGAAACAAG CGTTCCTGGA ATTAATTTAT AAATTTAATA AATCCCAATA TAATCCCAAA     2040

AAAAAAAAAA AAAAAATTCC TGCGGCCGCA AGGA                                2074
```

(2) INFORMATION FOR SEQ ID NO:12:

(i) SEQUENCE CHARACTERISTICS:
        (A) LENGTH: 325 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
Met Asp Gln Tyr Cys Ile Leu Gly Arg Ile Gly Glu Gly Ala His Gly
 1               5                  10                  15

Ile Val Phe Lys Ala Lys His Val Glu Thr Gly Glu Ile Val Ala Leu
                20                  25                  30

Lys Lys Val Ala Leu Arg Arg Leu Glu Asp Gly Phe Pro Asn Gln Ala
            35                  40                  45

Leu Arg Glu Ile Lys Ala Leu Gln Glu Met Glu Asp Asn Gln Tyr Val
        50                  55                  60

Val Gln Leu Lys Ala Val Phe Pro His Gly Gly Gly Phe Val Leu Ala
 65                  70                  75                  80

Phe Glu Phe Met Leu Ser Asp Leu Ala Glu Val Val Arg His Ala Gln
                85                  90                  95

Arg Pro Leu Ala Gln Ala Gln Val Lys Ser Tyr Leu Gln Met Leu Leu
            100                 105                 110

Lys Gly Val Ala Phe Cys His Ala Asn Asn Ile Val His Arg Asn Leu
        115                 120                 125

Lys Pro Ala Asn Leu Leu Ile Ser Ala Ser Gly Gln Leu Lys Ile Ala
    130                 135                 140

Asp Phe Gly Leu Ala Arg Val Phe Ser Pro Asp Gly Ser Arg Leu Tyr
145                 150                 155                 160

Thr His Gln Val Ala Thr Arg Ser Val Gly Cys Ile Met Gly Glu Leu
                165                 170                 175
```

```
Leu Asn Gly Ser Pro Leu Phe Pro Gly Lys Asn Asp Ile Glu Gln Leu
            180                 185                 190

Cys Tyr Val Leu Arg Ile Leu Gly Thr Pro Asn Pro Gln Val Trp Pro
        195                 200                 205

Glu Leu Thr Glu Leu Pro Asp Tyr Asn Lys Ile Ser Phe Lys Glu Gln
    210                 215                 220

Val Pro Met Pro Leu Glu Glu Val Leu Pro Asp Val Ser Pro Gln Ala
225                 230                 235                 240

Leu Asp Leu Leu Gly Gln Phe Leu Leu Tyr Pro Pro His Gln Arg Ile
            245                 250                 255

Ala Ala Ser Lys Ala Leu Leu His Gln Tyr Phe Phe Thr Ala Pro Leu
            260                 265                 270

Pro Ala His Pro Ser Glu Leu Pro Ile Pro Gln Arg Leu Gly Gly Pro
            275                 280                 285

Ala Pro Lys Ala His Pro Gly Pro Pro His Ile His Asp Phe His Val
            290                 295                 300

Asp Arg Pro Leu Glu Glu Ser Leu Leu Asn Pro Glu Leu Ile Arg Pro
305                 310                 315                 320

Phe Ile Leu Glu Gly
                325

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:13:

CCCAGTCACG ACGTTGTAAA ACG                                          23

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:14:

AGCGGATAAC AATTTCACAC AGG                                          23
```